United States Patent [19]

O'Neill

[11] Patent Number: 4,939,290

[45] Date of Patent: Jul. 3, 1990

[54] BENZOIC ACID DERIVATIVES

[75] Inventor: Brian T. O'Neill, Westbrook, Conn.

[73] Assignee: Pfizer Inc., New York, N.Y.

[21] Appl. No.: 275,449

[22] Filed: Nov. 23, 1988

[51] Int. Cl.$^5$ .................. C07C 211/45; C07C 225/18; C07C 225/16

[52] U.S. Cl. .................................. 560/110; 560/111; 562/405; 562/453

[58] Field of Search .................. 544/92; 560/110, 111; 562/403, 453

[56] References Cited

U.S. PATENT DOCUMENTS

| | | | |
|---|---|---|---|
| 4,521,616 | 1/1985 | Filfolt et al. | 562/456 |
| 4,563,459 | 1/1986 | Grohe et al. | 514/254 |
| 4,623,650 | 11/1986 | Gilligan et al. | 514/312 |

OTHER PUBLICATIONS

Streitwieser et al, Introduction to Organic Chemistry, 3rd Ed., pp. 163–166 and 181–183 (1985).
Eckert et al., Angew. Chem. Int. Ed. Engl., 26, 894–5 (1987).
Organic Syntheses Collective, vol. 3, 488–90 (1955).
Gauthier et al., Communications, 383–5 (1987).
Adv. in Het. Chem., 28, 127–182 (1981).
Cohen et al., Tetrahedron Letters, No. 2, 143–6 (1975).
Gowin, J. Chem. Soc. Perkin Trans. I, 1331–5 (1988).
Adv. Organometallic Chemistry, 12, 301–21 (1974).
Kappe et al., Advanced in Heterocyclic Chemistry, 28, 127–174 (1981).
Mitscher et al., J. of Med. Chem., 22, 1354–7 (1979).
Mitscher et al., J. of Med. Chem., 21, 485–9 (1978).
Lindley, Tetrahedron, 40, 1433–56 (1984).

*Primary Examiner*—Mukund J. Shah
*Assistant Examiner*—E. C. Ward
*Attorney, Agent, or Firm*—Peter C. Richardson; Paul H. Ginsburg; Gezina Holtrust

[57] ABSTRACT

Quinolonecarboxylic acid intermediaes useful in the preparation of antibacterial 6-fluouro-7-substituted-quinolonecarboxylic acids are prepared from 2-(iodo, bromo or chloro)-3-fluoro-4-(fluoro or chloro)-phenyl carboxylic acid or ester.

4 Claims, No Drawings

BENZOIC ACID DERIVATIVES

BACKGROUND OF THE INVENTION

The invention relates to intermediates useful in the preparation of 6-fluoro-7-halo-quinolonecarboxylic acid intermediates for the preparation of 6-fluoro-7-substituted-quinolonecarboxylic acids having antibacterial activity, and to processes for the preparation of such intermediates.

In general, the antibacterial 6-fluoro-7-substituted-quinolone-carboxylic acids are prepared by substitution of the corresponding 7-halo-6-fluoroquinolonecarboxylic acid intermediates wherein the halo atom is preferably fluoro or chloro. Prior art methods for preparing such 7-halo intermediates are described in U.S. Pat. Nos. 4,563,459 and 4,623,650.

SUMMARY OF THE INVENTION

The present invention relates to a novel process for the preparation of 7-halo-quinolonecarboxylic acid intermediates of the formula

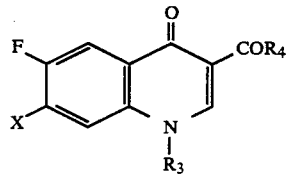

wherein $R_3$ is ethyl, t-butyl, cyclopropyl, phenyl, 4-fluorophenyl, or 2,4-difluorophenyl, $R_4$ is hydroxy, $C_1$-$C_4$ alkoxy, amino or $C_1$-$C_4$ alkylamino, and X is fluoro or chloro, and novel intermediates useful therein.

One class of intermediates of the invention are novel compounds of the formula

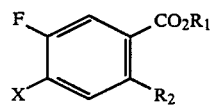

wherein $R_1$ is hydrogen or $C_1$-$C_4$ alkyl, $R_2$ is iodo, t-butylamino, cyclopropylamino, phenylamino, 4-fluorophenylamino, or 2,4-difluorophenylamino, and X is fluoro or chloro, with the proviso that when $R_2$ is iodo $R_1$ is hydrogen. Preferred intermediates within this class are compounds of formula V wherein $R_1$ is hydrogen, X is fluoro, and $R_2$ is iodo, cyclopropylamine, or 2,4-difluorophenyl.

Another class of intermediates of the invention are novel compounds of the formula

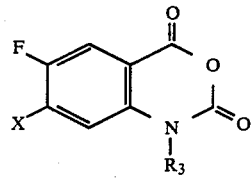

wherein X and $R_3$ are as defined above with reference to formula I.

According to the invention, compounds of the formula I are prepared by reacting a compound of the formula

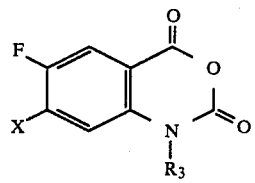

wherein $R_3$ and X are as defined above, with an alkali metal salt of a compound of the formula

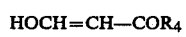

wherein $R_4$ is as defined above with reference to formula I.

The compounds of formula II are prepared, according to the invention, by reacting a compound of the formula

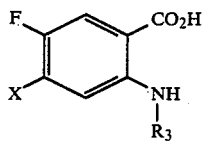

wherein X and $R_3$ are as defined above with a compound of the formula

wherein $R_5$ and $R_6$ are both chloro or trichloromethyloxy, or $R_5$ is chloro and $R_6$ is $C_1$-$C_6$ alkoxy, trichloromethyloxy, phenoxy, or phenoxy substituted by a substituent which is inert under the reaction conditions such as one, two or three of halo, nitro, $C_1$-$C_6$ alkyl, or trifluoromethyl. Preferably, $R_5$ and $R_6$ are both trichloromethoxy, or both chloro, or $R_5$ is chloro and $R_6$ is trichloromethyloxy.

The compounds of formula III are prepared, according to the invention, by reacting a compound of the formula

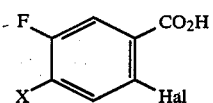

wherein X is fluoro or chloro, and Hal is iodo, bromo or chloro, with a compound of the formula $R_3NH_2$ wherein $R_3$ is ethyl, t-butyl, cyclopropyl, phenyl, 4-fluorophenyl, or 2,4-difluorophenyl, in the presence of copper or a copper compound.

The overall reaction to prepare compounds of formula I from compounds of formula IV through the above intermediate process steps for the preparation of compounds of formulas II and III, is also part of the invention.

DETAILED DESCRIPTION OF THE INVENTION

The compounds of formula IV wherein Hal is iodo are novel compounds. They may be prepared from the known compound 2-amino-4,5-difluoro benzoic acid by reaction with sodium nitrite in a solution of dilute sulfuric acid at a temperature of about $-10°$ to $0°$ C. and ambient pressure. The formed diazonium compound is then treated with a solution of potassium iodide in dilute sulfuric acid at a temperature between about $-10°$ to $0°$ C., and the resulting dark slurry stirred for about 12 to 24 hours on slow warming to ambient temperature.

The preparation of anthranilic acid compounds of the formula III from compounds of the formula IV proceeds in the presence of catalytic amounts of copper (0) or a copper compound such as cupric oxide or cuprous oxide, or a copper salt such as cupric acetate, cupric sulfate, cupric chloride, cupric bromide, cupric triflate, cuprous chloride, cuprous bromide, and cuprous triflate. The copper catalyst is generally present in amounts of at least about 5 mole %, and generally about 10 to 20 mole %. The reaction is in the presence of an inert, dipolar, aprotic solvent such as dimethylformamide, tetrahydrofurane, dimethoxyethane, N-methyl-pyrrolidinone, dimethyl acetamide or dimethyl sulfoxide, and in the presence of an organic base such as pyridine or dimethylaminopyridine in the optional presence of a tertiary amine base such as triethyl amine or diisopropylethyl amine. The organic base is generally present in amounts of 1 to 2 mole equivalents, usually 1.5 mole equivalent.

The reaction temperature depends on whether Hal in formula IV is iodo, bromo or chloro. When Hal is iodo, the reaction may be conducted at about $10°$ to $40°$ C., and advantageously at ambient temperature such as about $20°$ to $25°$ C. When Hal is bromo, the reaction temperature is from about $20°$ to $50°$ C. When Hal is chloro, the reaction temperature is about $50°$ to about $100°$ C., generally about $70°$ C., and the reaction is conducted in a sealed vessel causing a reaction pressure of between one atmosphere to about two atmospheres.

When Hal in formula IV is iodo or chloro, the reaction is at least initially in the absence of air, for instance by introduction of an inert gas such as nitrogen into the reaction vessel, or by conducting the reaction in a sealed vessel.

It was found that high yields are obtained by using about two mole equivalents of the reagent of the formula $R_3NH_2$, about 1.5 mole equivalents of the organic base pyridine in dimethyl formamide, and about 0.2 mole equivalent of the copper catalyst.

The reaction may also be conducted with one equivalent of $R_3NH_2$, one equivalent of copper or its salts and 1.5 equivalent pyridine in dimethyl formamide.

The isatoic anhydrides of formula II are prepared from compounds of formula III by reaction with a reagent of the formula $R_5R_6C=O$ wherein $R_5$ and $R_6$ are as defined above. For instance, the reagent is phosgene or, preferably, bis-(trichloromethyl)carbonate (triphosgene) which is commercially available and, as a solid, is easy to handle. When the above reagent is a solid, the reaction is conducted in an inert solvent such as a chlorinated alkane, e.g. methylene chloride, chloroform, carbon tetrachloride or dichloroethane, or an aromatic solvent such as toluene, benzene, or xylene. The reaction is conducted at about $-10°$ to $15°$ C. for about 15 minutes to 1.5 hours, usually for half an hour. When the reagent is phosgene, the solvent may also be an aqueous acid such as hydrochloric acid. When the reagent is a liquid such as methyl chloroformate or ethyl chloroformate, the solvent may be omitted and an excess of the reagent may be used instead. The reaction mixture is then heated between about $150°$ and $200°$ C. for about 18 to 24 hours.

The reaction to form the isatoic anhydrides of formula II is performed in the presence of an organic base such as pyridine or dimethylaminopyridine in the optional presence of a tertiary amine such as triethyl amine or diisopropylethylamine.

The quinolones of formula I are prepared from the isatoic anhydrides II by reaction with at least about one equivalent of the alkali metal salt of $C_1$-$C_3$-alkyl 3-hydroxyacrylate. The alkali metal is sodium, lithium or potassium. The reaction is conducted in a dipolar aprotic solvent such as dimethylformamide, tetrahydrofurane, dimethoxyethane, N-methylpyrrolidinone, or dimethylacetamide. The reaction temperature ranges from about $20°$ to $100°$ C., usually about $50°$ C., and the reaction time is about 1 to 24 hours, usually about 1 hour. The reaction is advantageously conducted in the presence of a chelating agent for alkali metal ions. Examples of suitable chelating agents are N,N'-dimethylimidazolidinone, hexamethyl phosphoric triamide, N,N'-dimethylpropylene urea, and tris[2-(methoxyethoxy)ethyl]amine.

The quinolones of formula I wherein $R_4$ is hydroxy may be prepared from the corresponding esters of formula I wherein $R_4$ is $C_1$-$C_4$ alkoxy by conventional hydrolysis, for instance by heating with an acid such as hydrochloric acid.

The following Examples illustrate the invention.

EXAMPLE I

To a 1 liter four neck round bottom flask equipped with mechanical stirrer, two dropping funnels and a thermometer was introduced 20 g (86.71 mmol) of 2-amino-4,5-difluorobenzoic acid and a solution of 12.3 ml concentrated sulfuric acid in 90 ml water. The slurry was cooled to between $0°$ and $-5°$ C. in an ice-acetone bath. One of the dropping funnels was charged with a solution of 6.57 g (95.22 mmol) sodium nitrite in 30 ml of water and slow addition of the solution was begun. The internal reaction temperature never rose above $0°$ C. and all the solution has been introduced after 5 minutes. The second dropping funnel was charged with a solution of 21.6 g (128.31 mmol) potassium iodide in 45 ml of 1N sulfuric acid. This solution was then added dropwise over a period of 10 minutes with the internal temperature at or below $0°$ C. During addition, the reaction mixture releases nitrogen gas which causes some foaming. Once the addition was completed, the dark mixture was stirred overnight while slowly warming to room temperature. The reaction mixture was quenched with a solution of 30 g of sodium bisulfite in 165 ml water and the suspension was adjusted to pH 2.5 with 5 ml of 6 N hydrochloric acid. The resulting slurry was stirred at $0°$ C. for 30 minutes and then filtered. Purification of the dark material was effected by dissolving the majority of the solid in ethyl acetate followed by clarification and treatment with activated charcoal. After filtration through a filter aid (celite) and evaporation there was obtained 20 g (82%) of 2-iodo-4,5-difluorobenzoic acid; m.p.: $126°$-$127°$ C.

EXAMPLE II

To a 35 ml single neck round bottom flask equipped with magnetic stir bar and nitrogen inlet was charged 45 mg (0.704 mmol) copper bronze, 5 ml of anhydrous dimethylformamide (DMF), 430 $\mu$l (5.28 mmol) of pyridine and 537 $\mu$l (7.75 mmol) cyclopropylamine. The resulting suspension was then treated with a solution of 1 g (3.52 mmol) 2-iodo-4,5-difluorobenzoic acid in 5 ml of DMF and the mixture was stirred overnight at room temperature. The reaction mixture, now a near solution, was clarified and then added to water (100 ml) at pH 4.5. A slurry forms immediately but before filtration the mixture was once again adjusted to pH 4.5 with 6N hydrochloric acid and cooled to 0° C. Filtration of the white solid afforded 0.720 g (95%) of 2-N-cyclopropylamino-4,5-difluorobenzoic acid; m.p.: 175°–176° C.

EXAMPLE III

To a 10 ml resealable pressure reaction flask equipped with a magnetic stirrer and teflon septum cap was charged a solution of 1.0 g (5.19 mmol) 2-chloro-4,5-difluorobenzoic acid, 792 μl (11.43 mmol) cyclopropylamine, 800 mg (4.15 mmol) copper(I) iodide and 630 μl (7.79 mmol) pyridine in 8.0 ml of N,N-dimethylacetamide. The flask was sealed and was heated to 70° C. during stirring for a period of 16 hours. The reaction mixture was allowed to cool to room temperature and was then added to 100 ml of water. The suspension was adjusted to pH 13 with sodium hydroxide solution and was stirred for 15 minutes at room temperature. The suspension was filtered and the filtrate was adjusted to pH 4.5 with concentrated aqueous HCl. Filtration of the resulting slurry provided 451 mg (41%) of 2-cyclopropylamino-4,5-difluorobenzoic acid; m.p.: 175°–176° C.

EXAMPLE IV

To a 10 ml single neck round bottom flask equipped with a septum and magnetic stirring bar was charged a solution of 100 mg (0.46 mmol) of 2-N-cyclopropylamino-4,5-difluorobenzoic acid and 62μl (0.44 mmol) of triethylamine in 2 ml of methylene chloride. The solution was cooled to 0° C. and was treated with a solution of 45 mg (0.147 mmol) bis-(trichloromethyl)-carbonate in 0.5 ml methylene chloride. Finally a catalytic amount of dimethylaminopyridine (10 mg) was introduced as a solution in methylene chloride (0.5 ml). After stirring at 0° C. for 1.5 hours, the reaction mixture was quenched by adding a small amount of 1N hydrochloric acid. The organic phase was dried over sodium sulfate and then concentrated to a yellow oil to afford 114 mg of N-cyclopropyl-6,7-difluoro-2H-3,1-benzoxazine-2,4(1H)dione (100%). The product was crystallized from hot ethanol; m.p.: 138°–139° C.

EXAMPLE V

To a 15 ml single neck round-bottom flask equipped with magentic stirrer and under nitrogen atmosphere was added 60 mg (0.484 mmol) of the sodium salt of methyl 3-hydroxyacrylate in 1.5 ml of DMF. The resulting solution was stirred in the presence of 4A molecular sieves overnight and then filtered into another reaction vessel fitted with condenser, nitrogen line and a magnetic stirrer. To the mixture was charged 52 μl (0.467 mmol) N,N'-dimethylimidazolidinone and the solution was heated to 55° C. To this reactor was added a solution of 93 mg (0.388 mmol) of N-cyclopropyl-6,7-difluoro-2H-3,1-benzoxazine-2,4(1H) dione in 1.5 ml of DMF. The reaction mixture was stirred at 55° C. for 1 hour. The system was allowed to cool to room temperature and was then added to 30 ml of water at pH 4.0. The pH of the resulting suspension was adjusted to 5.5 and the mixture was cooled to 0° C. and filtered. After drying there was obtained 50 mg (46%) of methyl 1-cyclopropyl-6,7-difluoro-1,4-dihydro-4-oxo-3-quinolinecarboxylate, m.p.: 223°–224° C. The filtrate was extracted with methylene chloride and after drying and evaporation there was obtained an additional 47 mg (43.5%, total yield: 89.5%) of the desired product.

EXAMPLE VI

A suspension of triethyl amine (15 ml, 0.11 mol), 2,4-difluoroaniline (25 ml, 0.24 mol), copper bronze (2.7 g., 0.04 mol), in hot DMF (25 ml) was treated with a solution of 2-chloro-4,5-difluorobenzoic acid (23 g., 0.12 mol) in 25 ml of DMF and the temperature was maintained at 85° C. for 8 hours. The reaction mixture was allowed to cool to room temperature and was then stirred overnight. The reaction mixture was evaporated in vacuo and the residue was partitioned between ether and aqueous ammonium chloride. The organic phase was washed with 2N HCl and saturated aqueous lithium chloride solution. The ether was dried over sodium sulfate, treated with darco and then filtered and evaporated. The residue was crystallized from hexane-ether to afford 21.6 g (62%) of 2-(2,4-difluorophenylamino)-4,5-difluorobenzoic acid; m.p.: 215°–216° C.

I claim:

1. A compound of the formula

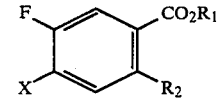

wherein $R_1$ is hydrogen or $C_1$-$C_4$ alkyl, $R_2$ is iodo, cyclopropylamino, phenylamino, 4-fluorophenylamino, 2,4-difluorophenylamino, or t-butylamino, and X is fluoro or chloro, with the proviso that when $R_2$ is iodo $R_1$ is hydrogen.

2. A compound according to claim 1 wherein $R_1$ is hydrogen, $R_2$ is iodo, and X is fluoro.

3. A compound according to claim 1 wherein $R_1$ is hydrogen, $R_2$ is cyclopropylamino, and X is fluoro.

4. A compound according to claim 1 wherein $R_1$ is hydrogen, $R_2$ is 2,4-difluorophenylamino, and X is fluoro.

* * * * *